United States Patent [19]
Henderson et al.

[11] Patent Number: 5,981,579
[45] Date of Patent: Nov. 9, 1999

[54] USE OF NITROVASODILATORS FOR TREATMENT OF DISEASE OR STRESS CONDITIONS IN A NON-HUMAN MAMMAL

[75] Inventors: Ian William Henderson, Sheffield; Karen Ann Hinckley, Chesterfield, both of United Kingdom

[73] Assignee: The University of Sheffield, United Kingdom

[21] Appl. No.: 08/793,419

[22] PCT Filed: Aug. 25, 1995

[86] PCT No.: PCT/EP95/03367

§ 371 Date: Jun. 16, 1997

§ 102(e) Date: Jun. 16, 1997

[87] PCT Pub. No.: WO96/05816

PCT Pub. Date: Feb. 29, 1996

[30] Foreign Application Priority Data

Aug. 25, 1994 [GB] United Kingdom .................. 9417347

[51] Int. Cl.$^6$ .................................................. A61K 31/21
[52] U.S. Cl. ........................................... 514/509; 424/608
[58] Field of Search .............................. 514/509; 424/608

[56] References Cited

U.S. PATENT DOCUMENTS

| | | | |
|---|---|---|---|
| 4,777,047 | 10/1988 | Bauer et al. .............................. | 424/449 |
| 5,132,115 | 7/1992 | Wolter et al. ............................ | 424/448 |
| 5,189,986 | 3/1993 | Burkoth ................................... | 119/156 |

FOREIGN PATENT DOCUMENTS

| | | |
|---|---|---|
| 0441119A2 | 8/1991 | European Pat. Off. . |
| 4305881C1 | 3/1994 | Germany . |
| 364045 | 8/1930 | United Kingdom . |
| 2021950 | 12/1979 | United Kingdom . |
| 2281207 | 3/1995 | United Kingdom . |
| 2281208 | 3/1995 | United Kingdom . |
| 2292520 | 2/1996 | United Kingdom . |
| WO8606281 | 11/1986 | WIPO . |
| 9418966 | 9/1994 | WIPO . |

OTHER PUBLICATIONS

Tillman, L.G., et al., "Serum angiotensin converting enzyme activity and response to angiotensin I in horses", *Equine Colic*, pp. 80–83, 1990.
Bryant, Clare E., et al., "Nitric Oxide: friend or foe?", *Equine Veterinary Education*, 1994, pp. 59–64.
Young, Stephen, "The Body's Vital Poison,"*New Scientist*, Mar. 13, 1993, pp. 36–40.
British National Formulary 25, No. 25, Mar. 1993, "2.5.5 Angiotensin–converting enzyme inhibitors", "Captopril", pp. 87–88.
Purohit, Ram C., et al., "Evaluation of Vasoactive Drugs in Equine Hypertension and Laminitis", Proceedings of First Equine Endotoxaemia Meeting, Sep. 1981. pp. 152–159.
*Monthly Index of Medical Specialities*, Aug. 1992, "Hypertensive", pp. 46–63, 1992.
Dhanakoti, Srinivas N., et al., "Net Renal Arginine Flux in Rats Is Not Affected by Dietary Arginine or Dietary Protein Intake", American Institute of Nutrition, pp. 1127–1134, 1992.

Brusilow, Saul, "Treatment of Urea Cycle Disorders," *Treatment of Genetic Diseases*, ed. Deswick R.J., 1991, pp. 79–95, published Churchill Livingston, New York.
Galey, F.D., et al., "Antagonism in isolated equine digital vessels of contraction induced by epinephrine in the presence of hydrocortisone and an aqueous extract of black walnut," *J. Vet. Pharmacal. Therap.* 12:411–420, 1989., pp. 411–419.
Martindale—The Extra Pharmacopoeia, 29th Edition, ed. by James E.F. Reynolds, London, The Pharmaceutical Press, "Antihypertensive Agents," pp. 466–504, 1989.
Martindale—The Extra Pharmacopoeia, 29th Edition, ed. by James E.F. Reynolds, London, The Pharmaceutical Press, "Arginine", p. 1254, 1989.
Martindale—The Extra Pharmacopoeia, 29th Edition, ed. by James E.F. Reynolds, London, The Pharmaceutical Press, "Captopril", p. 468, 1989.
Martindale—13th Edition, London, The Pharmaceutical Press, "Glyceryl Trinitrate" pp. 1020–1023, 1992.
Martindale—13th Edition,, London, The Pharmaceutical Press, "Arginine", pp. 1035–1038, 1992.
Martindale—13th Edition,, London, The Pharmaceutical Press, "Sodium Nitroprusside", pp. 387–389, 1992.
The Merck Index, 11th Edition, ed. by Susan Badavari, Merck & Co., Inc., Rahway, NJ, 1989, "Captopril," pp. 267–268, 1989.
The Merck Index, 11th Edition, ed. by Susan Badavari, Merck & Co., Inc., Rahway, NJ, 1989, "Arginine", p. 808, 1989.
Yelle, Marianne, "Clinicians guide to equine laminitis," *Equine Veterinary Journal*, 1986, pp. 156–158.
Nickerson, Mark, "Vasodilator Drugs", *The Pharmacological Use of Therapeutics*, pp. 745–764, 1970.
Abstract: Miller, Warren G., "Acute Equine Laminitis: Renal Morphology and Endocrine Interplay", Texas A&M, 1981.
Abstract: Rossitich, E. Jr., "L–arginine normalizes endothelial function in cerebral vessels from hypercholesterolemic rabbits", J–Clin–Invest, Apr. 1991, 87(4):1295–9.
Abstract: Tillman, L.G., et al., "Serum angiotensin converting enzyme activity and response tot angiotensin in I in horses," Dept. of Pharmaceutics, College of Pharmacy, University of Georgia, Athens, *Equine Veterinary Journal* (Supp. 7) pp. 80–83, 1989.
Colles, Dr. Chris, "Laminitis Research", *Equine Veterinary Journal*, vol. 23 (1981), pp. 237–238.
Brosnan, J.T., et al., Department of Biochemistry, Memorial University of Newfoundland, St. Johns., Newfoundland, Canada, A1B 3X9, "Endogenous Arginine Synthesis", 1992.
"Laminitis," *Adam Lameness in Horses*, 4$^{th}$ Edition, ed. Stashak TS, Lea & Febiger of Philadelphia, pp. 493–495, 1993.

*Primary Examiner*—William R. A. Jarvis
*Attorney, Agent, or Firm*—Sheldon & Mak

[57] ABSTRACT

This invention relates to methods of treating or controlling a disease or stress condition such as laminitis in a non-human mammal by topically applying to the limb of the mammal a nitrovasodilator and a protective covering dressing in the form of a cuff, sleeve, or boot.

6 Claims, 3 Drawing Sheets

ANTERIOR VIEW

POSTERIOR VIEW

USE OF NITROVASODILATORS FOR TREATMENT OF DISEASE OR STRESS CONDITIONS IN A NON-HUMAN MAMMAL

This application is a 371 of PCT/EP95/03367, filed Aug. 25, 1995.

FIELD OF THE INVENTION

This invention relates to the treatment of disease in animals and is more particularly concerned with a novel pharmaceutical pack and a novel form of treatment for various non-human mammalian diseases and distress conditions.

BACKGROUND TO THE INVENTION

Various form of systemic treatment are prescribed for animals in diseased or distressed conditions. Such treatments involve the administration of medicaments by intravenous, intramuscular or parenteral infusion or injection, by oral administration or by suppositories. However, for a number of animals the prescribed treatments are not easy to administer, particularly if the animal will not eat, or is required to remain still for long periods of time. In other cases the systemic treatments hitherto proposed have been found to be relatively ineffective, especially in relation to diseases of the legs and feet, and systemic and local vascular disorders, or to have undesirable side effects.

SUMMARY OF THE INVENTION

According to the present invention, an animal suffering from a disease or distress condition, or which is liable to suffer therefrom, or susceptible thereto, is treated with an agent active in controlling or preventing such a condition in a composition formulated for topical application.

In a first aspect, the invention provides a pack comprising an active agent for the treatment, prevention, or control of a disease or distress condition comprising:
  laminitis;
  acute equine rhabdomylosis or azoturia;
  navicular disease,
  chronic obstructive pulmonary disorder (COPD);
  exercise Induced pulmonary haemorrhage (EIPH);
  loss of libido in breeding stallions; and/or
  vascular and myometrial complications associated with pregnancy,
in a non-human mammal, which comprises a protective covering and/or dressing and a composition comprising the active agent formulated for topical application.

In another aspect, the invention provides a method for the treatment, prevention or control of a disease or distress condition comprising:
  laminitis;
  acute equine rhabdomylosis or azoturia;
  navicular disease;
  chronic obstructive pulmonary disorder (COPD);
  exercise induced pulmonary haemorrhage (EIPHI);
  loss of libido in breeding stallions; and/or
  vascular and myometrial complications associated with pregnancy,
in a non-human mammal, which comprises the topical application of a composition comprising an active agent for the treatment, prevention, or control of the disease or distress condition, said composition being provided with a protective covering and/or dressing.

In a further aspect, the invention provides the use of an active agent for the treatment, prevention, or control of a disease or a distress condition comprising:
  laminitis;
  acute equine rhabdomylosis or azoturia:
  navicular disease;
  chronic obstructive pulmonary disorder (CORD);
  exercise induced pulmonary haemorrhage (EIPH);
  loss of libido in breeding stallions; and/or
  vascular and myonetrial complications associated with pregnancy,
in a non-human mammal, for the manufacture of a pack comprising a protective covering and/or dressing and a topically applied medicament for the treatment of such disease or distress condition.

DETAILED DESCRIPTION OF THE INVENTION

A pack in accordance with the present invention is preferably adapted to provide a unidirectional outflow of the active agent into the vasculature of the animal and can comprise, for example, a protective covering, which may be a tape or bandage comprising a plastics film or sheet, or a woven or non-woven natural or synthetic fibrous material. The protective covering is preferably flexible and may be resilient or elasticated as appropriate. In preferred embodiments the protective covering comprises an opaque material or other shielding means for protecting the active agent from light rays and/or sunlight.

Preferably the protective covering is provided with means for securing the protective covering to the animal, which means may comprise an adhesive layer coated onto the protective covering, or a layer of Velcro or similar material. Alternatively, the securing means may comprise an adhesive tape or a Velcro cuff or bandage. For use on the legs or feet, the protective covering may comprise a protective boot. For use on the tail, the protective covering may comprise a cuff or sleeve.

The dressing may comprise a gauze, or non-woven pad of fibrous material, and in certain embodiments preferably has absorbent characteristics. The gauze or absorbent pad may be provided with a perforated plastics film layer on the side which is to be in contact with the animal.

In the simplest case, the composition may be provided in a separate container, for example a tube, ampoule, or similar dispenser, applied to the animal topically as appropriate, and then covered with the protective covering and/or dressing. In another, preferred, embodiment, however, the pack comprises an absorbent pad pre-impregnated with the composition comprising the active agent, which is applied to the animal and covered with the protective covering. In this embodiment, the absorbent pad and protective covering may be supplied, for example, in a foil container or similar protective package.

In a still further preferred embodiment, the pack may include a protective covering comprising a rigid or flexible plastics cuff or sleeve provided with a catheter or other reservoir which can be wholly or partly enclosed by the cuff or sleeve and filled through an external port. In this embodiment, the active agent can be "topped up" or the catheter or other reservoir re-filled without removing the cuff or sleeve. The active agent in this embodiment of the pack can be provided in an ampule containing a solution of the active agent in an appropriate liquid vehicle.

The composition of thee invention preferably comprises a systemic active agent, which can be dispersed in a lipophilic or fat soluble material or vehicle. The active agent Is preferably itself lipophilic, or is a lipophobic material which has been rendered lipophilic. The active agent is preferably present in the composition in an amount of from 0.5% to 10% by weight, more preferably about 2% by weight, based upon the weight of the composition.

Certain of the treatments disclosed in the present application are novel methods, for example the use of nitrovasodilators such as glyceryl trinitrate for the treatment of laminitis, acute equine rhabdomylosis, navicular disease, chronic obstructive pulmonary disorder, exercise induced pulmonary haemorrhage, loss of libido in breeding stallions, and vascular and myometrial complications associated with pregnancy, and this is accordingly a further aspect of the invention.

It is an important feature of the present invention that the active agents used, whilst formulated for topical application, have a systemic action. Thus the active agent need not necessarily be applied at the site exhibiting the symptoms of the disease, although in some cases this may be advantageous.

The invention is particularly applicable to the treatment of diseases affecting the legs and/or feet of animals, and will henceforth be more particularly described with reference to the treatment of laminitis. From the foregoing discussion, however, it will have been understood that the invention is not limited thereto and is of general applicability to the diseases and distress conditions in animals hereinbefore specified.

Laminitis is a disease affecting the peripheral vasculature of the feet in hoofed animals. It is common in cattle and horses, and is a major cause of temporary and permanent lameness. Laminitis can be extreme in horses and euthanasia is often justified. The severity of the disease varies but can be most severe in horses because of the anatomical arrangement of the vasculature within the equine hoof. Cattle and horses have a high incidence of the disease which results in considerable economic losses.

The pathophysiology of the developmental, acute and chronic stages of the disease are not known. However, the pathogenesis of the condition in all species seems to be similar. For example, there is a strong association between dietary habits and the onset of the disease. The nutritional aspects of laminitis are akin in both horses and cattle; high protein and/or carbohydrate diets are etiological factors in the condition.

In a review of the concepts and current therapy of the condition, Yelle in Equine Veterinary Journal (1986) 18, 156–158 concluded that laminitis should be considered as an emergency condition requiring immediate therapy. The acute phase of the disease may be protracted and incur large expenses usually with a poor prognosis. Many laminitic horses require life long attention. A variety of treatments are proposed, including local nerve blocks and systemic analgesics to control pain, antibiotics to control infection, non-steroidal anti-inflammatory drugs (NSAIDs) to reduce inflammation and padding to maintain local hoof integrity.

Nevertheless, as will be appreciated from the above, there is still no effective treatment for laminitis which continues to cause considerable suffering in animals and substantial expenses to their owners.

Laminitis affects the dermal laminae, soft tissues situated beneath the horny exterior of the hoof. It has been suggested that, although during episodes of the disease the total blood flow to the hoof is increased, reduced perfusion occurs in the dorsal laminae. It has been speculated that the reduced perfusion may be caused by vasoconstriction of arterioles, or opening of arteriovenous shunts, or that increase in post-capillary resistance may raise capillary pressure and disrupt the normal microvascular fluid dynamics leading to oedema and reduced perfusion.

By monitoring blood oxygenation levels in the dermal laminae, we have now discovered that the outset of laminitis is accompanied by haemostasis in the hoof.

The invention accordingly provides in a further aspect a method for delaying or substantially preventing the onset of laminitis in susceptible animals, or for improving the condition if present, which comprises the topical administration of certain effective compounds in an amount sufficient to overcome haemostasis, initiate reperfusion and improve blood oxygenation within the dermal laminae.

Also included within the invention is a pharmaceutical pac for the treatment of laminitis which comprises a protective covering or dressing and a pharmaceutical composition comprising a compound effective to overcome haemostasis, initiate reperfusion and improve blood oxygenation within the dermal laminae, formulated for topical application.

In a still further aspect, the invention provides the use of a compound effective to overcome haemostasis, initiate reperfusion and improve blood oxygenation within the dermal laminae in the manufacture of a topically applied medicament for the treatment of laminitis.

The preferred compounds effective to overcome haemostasis, initiates reperfusion and improve blood oxygenation within the dermal laminae are compounds capable of reducing vasconstriction and/or of inducing vasodilstation, and particularly peptide and non-peptide vasodiltors which also antagonise the action of vasoconstrictors. The preferred compounds also, or alternatively, inhibit the synthesis of endothelin, a potent vasoconstrictor synthesised by endothalial cells.

Particularly preferred compounds includes, for example, nitrovasodilators, for example, glyceryl trinitrate and sodium nitroprusside, and other compounds such an acetylcholine and 5-hydroxytryptamine (serotonin) which stimulate endothelial cells to produce "endothelium derived relaxing factors". Peptide vasodilators include, for example, atrial natriuretic peptide, bradykinin, brain natriuretic peptide and C-natriuretic peptide.

The vasodiltors is preferably topically applied, in a suitable vehicle, to, for example, the skin of the pastern adjacent to the affected region of the hoof preferably hair is removed from a portion of skin and the vasodilator is applied thereto and covered with a protective covering or dressing in the form of a patch. The patch may, for example, have a gauze, or dressing, or a permeable re-fillable capsule for receiving the vasodilator, and an adhesive-coated protective and light-excluding backing layer, which keeps the gauze, dressing, or capsule in constant contact with the skin.

Preferably the vasodilator is applied close to the superficial vasculature of the animal, for example, in the case of an equine species, to the skin adjacent to one or more of the pasterns, the cannon bones, proximal to the carpal or tarsal joints, or the ventral aspect of the tail.

It has previously been proposed to apply certain medicaments to the ear of an animal for purposes unrelated to the present invention, but this is not preferred herein as it is very difficult, if not impossible, to provide a protective covering or dressing which can effectively exclude light (which can render active agents inactive) from this site of application without causing the animal further stress.

The vasodilator can be dispersed in a lipophilic or fat soluble vehicle which can be a liquid, gel, emollient or paste. Suitable vehicles include, for example, glycerol, petroleum jelly, petroleum, and dimethyl sulfoxide. Dimethylsulfoxide is particularly preferred as it can also act as a free radical scavenger.

For mild attacks of laminitis, topical application of a vasodilator to the affected feet as hereinbefore described may be sufficient, although for more severe or acute episodes it is preferred to combine topical application of the vasodilator with systemic administration of 1-arginine or a pre-cursor of the biosynthesis thereof, as described in our co-pending International Patent Application No. PCT/EP94/02819 and UK Patent Application No. 9317943.0, the entire disclosures of which are incorporated herein by reference for all purposes.

A suitable vasodilator-containing composition for topical administration may comprise, for example, from 0.5 to 10% by weight of the vasodilator, based on the weight of the composition, preferably about 2% by weight. The composition may be applied as a thin layer to an area of tissue, to give a daily dose of from 0.005 to 1.0, preferably 0.01 to 0.8mg/kilogram body weight, and then covered with a patch as previously described. Alternatively, the patch may comprise an absorbent layer which can be pre-impregnated with the vasodilator. A typical patch may comprise from 5 to 120 mg of vasodilator and the patches may be changed up to four times or replenished with vasodilator in a liquid medium as appropriate. One limb alone can be treated, for example, after orthopaedic surgery on the contralateral limb and in this case the dose can be up to 30 mg of vasodilator per limb.

Whilst the invention has been specifically described in relation to laminitis, the use of therapeutically active compounds which are capable of reducing vasoconstriction, and/or inducing vasodilatation, for example, nitrovasodilators, is also suitable for the treatment of the other conditions hereinbefore specified.

Acute equine rhabdomylosis or azoturia is characterised by an accumulation of lactic acid in skeletal muscle after exercise and can result in muscle damage. It is postulated that compromised blood flow in response to metabolic demands is responsible for this dysfunction, and the application of a therapeutically active compound capable of reducing vasoconstriction, and/or inducing vasodilatation, to the affected area, or to the skin elsewhere, in accordance with the invention, can provide an appropriate prophylactic treatment.

Navicular disease is characterised by bone resorption around the foraminae of the distal sesamoid bones (navicular bone) of the front limbs of equine species. This is the result of compromised blood flow through the vessels within the bone. The application of a therapeutically active compound capable of reducing vasoconstriction, and/or inducing vasodilatation in accordance with the invention, can be an effective treatment for this condition.

Chronic obstructive pulmonary disorder (COPD) is caused by allergic responses to allergens, for example, dust or mould spores. Effected animals cough, "wheeze", and have laboured breathing. The application of a therapeutically active compound which is capable of reducing vasoconstriction, and/or inducing vasodilatation, in accordance with the invention, can be an effective treatment for this condition.

Exercise induced pulmonary haemorrhage (EIPH) is a condition wherein pulmonary bleeding occurs during strenuous exercise, and particularly affects race horses. The application of a therapeutically active compound which is capable of reducing vasoconstriction, and/or inducing vasodilatation, in accordance with the invention, can be an effective prophylactic treatment for this condition, and, for example, a patch or patches comprising the active agent may be applied to a race horse immediately before training gallops or races.

Loss of libido (impotence) in breeding stallions can be a major problem for stud farms. The use of a therapeutically active compound which is capable of reducing vasoconstriction, and/or inducing vasodilatation, for example, applied under a cuff or sleeve around the tail of the effected animal, can be an effective treatment vascular and myometrial complications associated with pregnancy can also be effectively treated by the application of a therapeutically active compound which is capable of reducing vasoconstriction and/or inducing vasodilation in accordance with the invention, for example, by applying the active agent under a cuff or sleeve around the tail of the animal, or by any other convenient means as described herein Whilst the invention is not limited to any particular theory, it is believed that, in at least some applications, the action of the active agent may be to reduce the synthesis of endothelins, which are the most potent endogenous vasoconstrictors known, and are implicated in many vascular diseases.

Preferred embodiments of packs according to the invention will now be described, by way of example only, with reference to the accompanying Drawings, in which;

Figure 1:
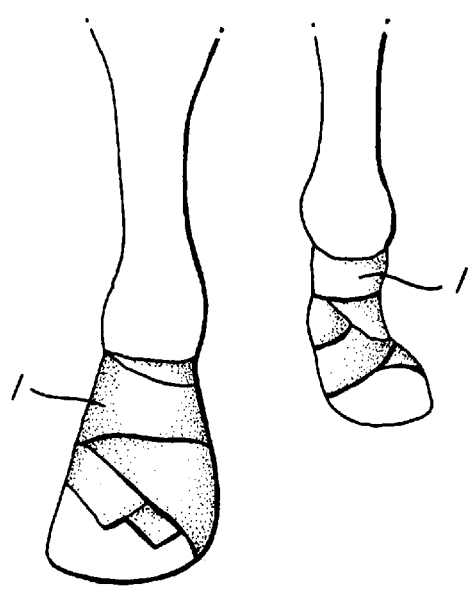
FIG. 1 shows a photograph of elasticated bandage "patches" in place on the pasterns of a horse.

Referring now to the drawings, in FIG. 1 the patches 1 are formed by wrapping an elasticated bandage repeatedly around each of the pasterns of the horse. A gauze or absorbent pad (not shown) is positioned beneath each elasticated bandage and in contact with the skin of the pasterns.

Figure 2:
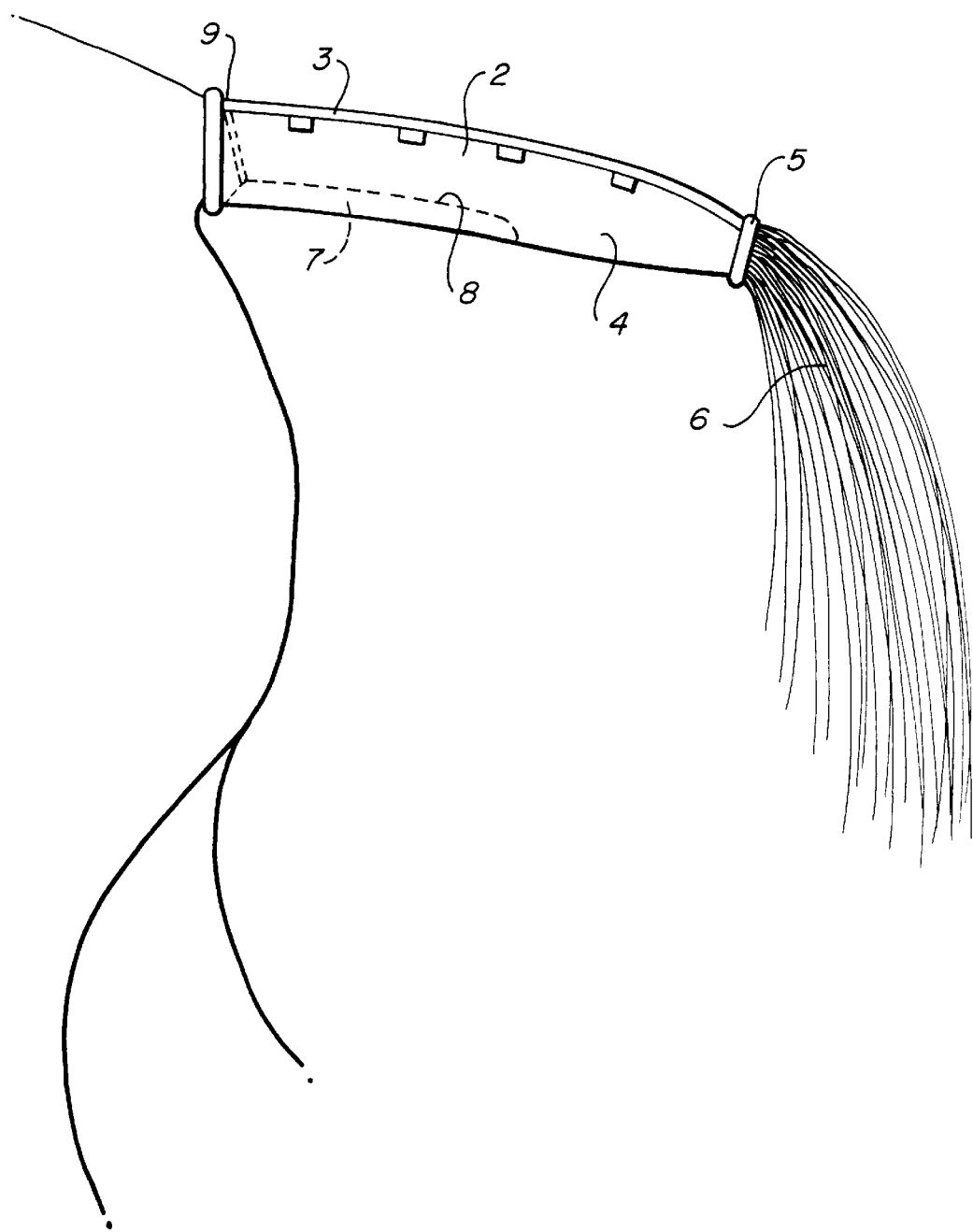
FIG. 2 shows a diagrammatic representation of an elasticated bandage "patch" in place on the tail of a horse.

In FIG. 2 the "patch" comprises an elasticated cuff 2 having a semi rigid spine 3 which rests on the upper surface of the tail 4 but allows side movement. A clasp 5 at the end of the cuff 2 surrounds the tail hair 6 only. A reservoir 7 for the active agent is positioned in contact with the ventral aspect 8 of the tail and is supplied through a port 9.

Figure 3A:
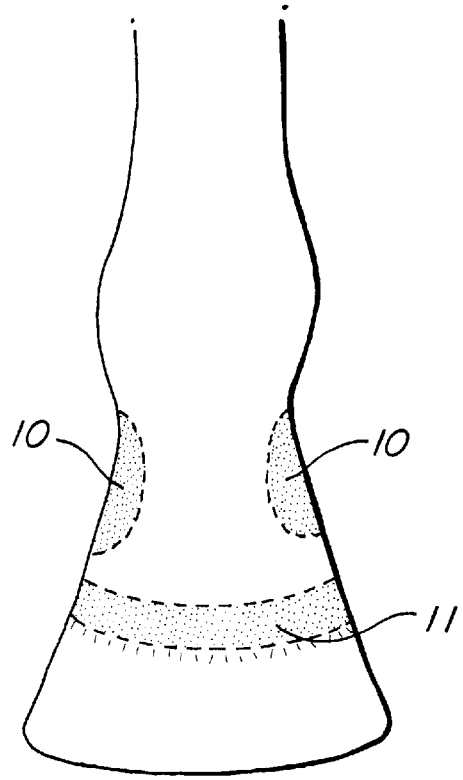
FIGS. 3(a) and (b) shows diagrammatically the preferred sites for percutaneous delivery of the active agent according to the invention into the pedal vasculature of the equine limb.
Figure 3B:
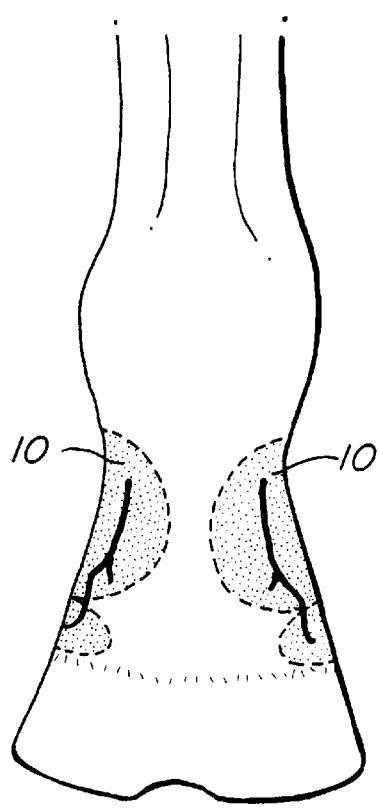

FIGS. 3(a) and (b) illustrates the preferred sites for delivery of active agents into the pedal vasculature of the equine limb. Two primary areas are accessible: the digital vessels which supply the interior of the hoof; and the coronary band supplying the more peripheral areas which perfuse the tissues responsible for hoof growth.

Figure 4:
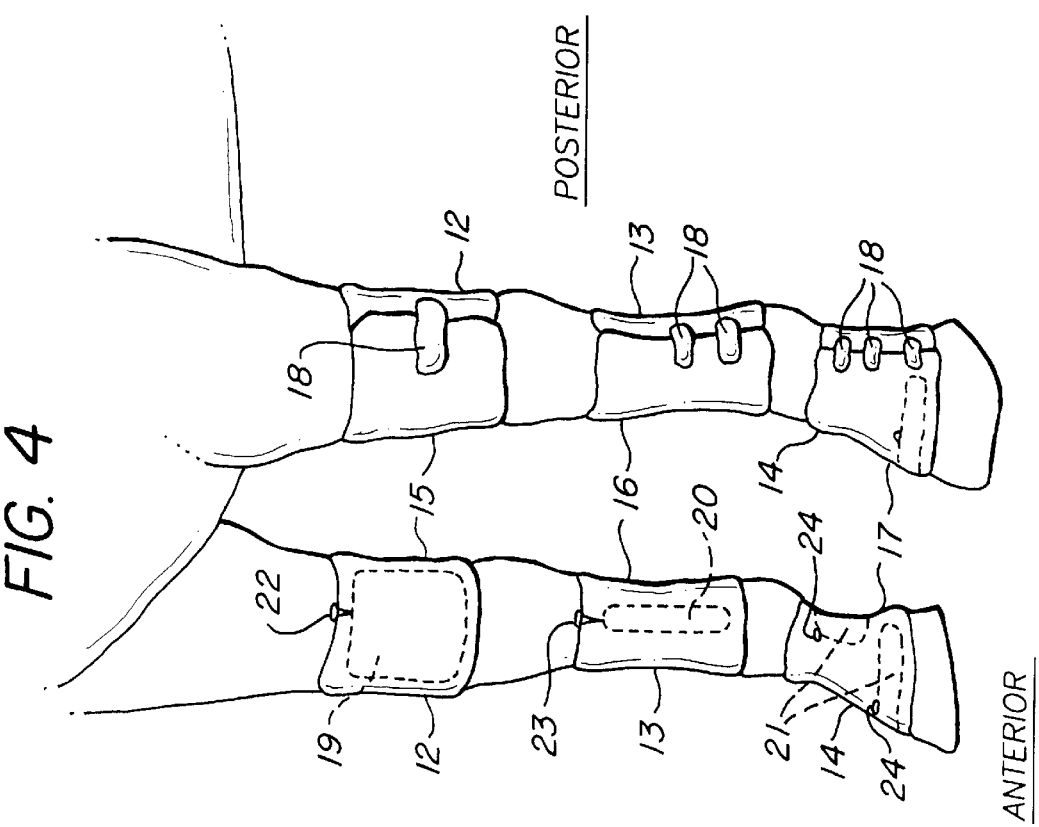
FIG. 4 illustrates diagrammatically three transdermal sites provided with boots or sleeves for the delivery of active agents to the equine limb.

FIG. 4 illustrates cuffs, sleeves, or boots applied to three areas 12, 13, 14, of the equine limb. Each cuff, sleeve, or boot 15, 16, 17, may be fastened by a fastener 18 to a key vascular area to give optimal delivery of the active agent and may incorporate one or more reservoirs 19, 20, 21 to contain the active agent. The latter may be replenished at intervals as necessary through ports 22, 23, 24.

Figure 5:
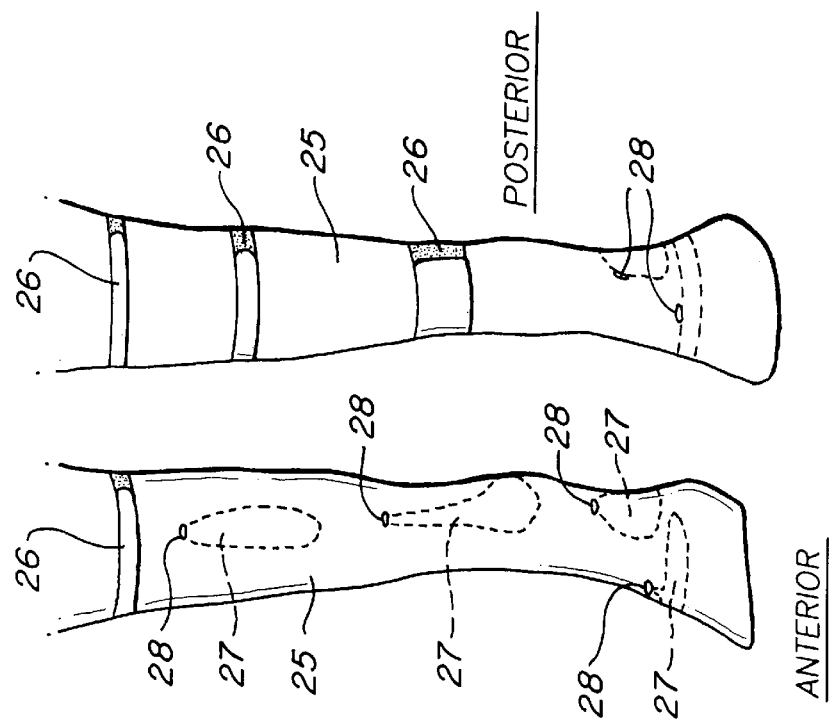
FIG. 5 shows a multiple delivery system in the form of a "stocking" or full boot for the limb of a horse.

FIG. 5 illustrates a multiple delivery system in the form of a "stocking" or full boot 25 for the horse's limb. The system resembles that shown in FIG. 4 but is formed as a single item. It may have a Velcro fastening 26 and incorporate reservoirs 27 and filling ports 28.

The invention is particularly suitable for the treatment of cattle and horses, and is of particular value in the treatment of artiodactyls and perissodactyls, for example, equine breeds, donkeys, zebras and camelids.

The invention is illustrated by the following Examples:

EXAMPLES 1

This Example describes the treatment of a horse suffering from laminitis with a nitrovasodilator, glyceryl trinitrate, in accordance with the invention.

The caudal surface of the pasterns of a horse suffering from laminitis were clipped over the area of digital vessels extending medially and laterally. An area of skin about 1.25 cm to 5cm on each pastern was exposed. The paths as described below were gently secured on the pasterns so that they were positioned over digital vessels when in place. In two cases the untreated right hindlimb was bound with a dummy patch without glyceryl trinitrate, and served as a "control".

Glyceryl Trinitrate Ointment

2% Glyceryl Trinitrate ointment (Percutol, Cusi (UK) Limited, Haslemere, Surrey) is applied once daily to the pasterns as a "patch"; each aliquot of paste positioned over the digital vessels, covered with grease proof paper and secured in place with adhesive tape (Treatplast, UK).

The dose of glyceryl trinitrate paste is measured in inches on a marked sheet:

2.54 cm paste weighs 0.672 g contains 14.4mg of glyceryl trinitrate 1.90 cm paste weighs 0.504 g contains 10.8mg of glyceryl trinitrate 1.27 cm paste weighs 0.336 g contains 6.72mg of glyceryl trinitrate 0.63 cm paste weighs 0.168 g contains 3.36 g of glyceryl trinitrate a) An 18 year old Welsh cross pony mare, with a history of laminitis in previous years developed spontaneous laminitis whilst at grass. This pony was stabled when laminitis became apparent. The pony had been injured in a collision with another pony in the field and was receiving 1 g phenylbutazone daily orally for two weeks before the onset of laminitis, and this was continued throughout the treatment. The mare was treated with glyceryl trinitrate patches and analgesic therapy was given one hour after application of the patches. The administration of glyceryl trinitrate was given as follows:

Initial dose of glyceryl trinitrate 21.6 mg/limb/day giving a total dose 64.8 mg/day.

The initial dose was 0.3 mg/kg/day for one day.

Reduced doses i. 10.8 mg/limb total dose 32.4 mg/day reduced dose was 0.13 mg/kg/day for one day.

ii. 13.44 mg/limb total dose 40.32 mg/day reduced dose was 0.16 mg/kg/day for two days.

Withdrawal dose 6.72 mg/limb total dose 20,16 mg/day withdrawal dose was 0.01 mg/kg/day for two days.

Glyceryl trinitrate patches applied to the pasterns of three limbs reduced bounding digital pulses and improved lameness in the treated limbs and reduced systemic blood pressure in a dose related fashion. A rapid reduction in the dose an the second day caused an increase in blood pressure and worsening of lameness in all limbs: this was reversed with an increased dose. There seemed to be a direct relationship between the dose of glyceryl trinitrate and mean blood pressure. No difference was seen in treated and untreated limbs but this may have been masked by stiffness in the pony resulting from her accident several weeks previously. The pony improved steadily and was turned to grass one week later.

In other cases topical application of glyceryl trinitrate patches to the shaved pasterns of ponies suffering acute laminitis reduced systemic blood pressure, attenuated the bounding digital pulses and improved lameness of treated limbs. The doses given are shown in Table 1. Glyceryl trinitrate ointment (2%) (Percutol, Cusi (UK) Ltd., Haslemere, Surrey) was usually administered as an initial dose of 60 mg (0.3 mg/kg/day) for two days (dose a). If blood pressure decreased and lameness improved, the dose was reduced to 40 mg glycerol trinitrate/day (0.02 mg/kg/day) for two days (dose b) and then to 20 mg (0.01 mg/kg/day) for two days until the end of the treatment (dose c). This regime varied slightly according to individual responses and severity of the disease. Clinically, the ponies seemed brighter and happier when the blood pressure was reduced and lameness improved markedly. Indeed, a pony that had suffered a severe attack was able to trot on concrete within days of his attack. No analgesics were required. In all cases there were no obvious secondary changes in the hooves and no necrosis apparent. The untreated mild cases did not show such a dramatic improvement although a pony that had been treated with glyceryl trinitrate patches in a previous attack improved more quickly than a pony that had not been treated before.

EXAMPLE 2

A pony suffering from severe acute laminitis is treated with glyceryl trinitrate patches as described in Example 1. The treatment and results are given in Table 2.

EXAMPLE 3

Glyceryl trinitrate and dimethyl sulphoxide (DMSC) combined as transdermal treatment for acute laminitis The procedures of Examples 1 and 2 are repeated using doses of glyceryl trinitrate as described therein, combined with DMSO which acts as a free radical scavenger and anti-inflammatory agent. The amount of DMSO administered depends on the size and body weight of the animal. The combined treatment aids the prevention of reperfusion injury during vasodilation.

EXAMPLE 4

Glyceryl trinitrate as transdermal treatment for chronic obstructive pulmonary disorder (COPD)

Glyceryl trinitrate (GTN) patches were administered to a laminitic pony suffering from COPD as described in Examples 1 and 2. It was noticed that the respiration markedly improved (easier breathing and absence of "wheezing"), alongside an improved gait and a modest reduction in blood pressure. The given dose of GTN of 53.76 mg in total was repeated for 2 days and then a withdrawal dose instigated, as shown In Table 1. Marked improvement was seen within 3 days.

EXAMPLE 5

Glyceryl trinitrate as transdermal treatment for exercise induced pulmonary haemorrhage (EIPH)

EIPH occurs when bleeding in the lungs happens during exercise. It is commonplace in racehorses and is the cause of many fatalities. GTN patches can be applied to the horse as described in Examples 1 and 2 as a prophylactic treatment before training or racing.

EXAMPLE 6

Transdermal GTN as a general purpose vasodilator in horses

Transdermal GTN "patches" at the doses shown in table 2 are applied to horses and ponies to treat navicular disease, a vasospastic/vasoconstrictive condition of distal sesamoids.

At larger doses, similar preparations of GTN can be applied to the limbs to offset vascular and myometrial complications associated with some pregnancies towards term.

EXAMPLE 7

Transdermal GTN "patches" as described in Examples 1 and 2 are applied to stallions in cases of loss of libido, and can lead to a significant observed improvement in the condition. The dose is as dose (a) in Table 1, repeated at up to four times daily.

The reader's attention is directed to all papers and documents which are filed concurrently with this specification and which are open to public inspection with this specification, and the contents of all such papers and documents are incorporated herein by reference.

All the features disclosed in this specification (including an accompanying claims, abstract and drawings), and/or all of the steps or any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed In one example only of a generic series of equivalent or similar features.

The invention is not restricted to the details of the foregoing embodiment(s). This invention extends to any novel one, or any novel combination, of the features disclosed in this specification (including any accompanying claims, abstract and drawings), or to any novel one, or any novel combination, of the steps of any method or process so disclosed.

TABLE 1

Doses of glyceryl trinitrate given to actuely laminitis ponies

| Approximate weight of glyceryl trinitrate | Total amount of Glycerly trinitrate (mg)/day Applied in two aliquots to: | | | | |
|---|---|---|---|---|---|
| paste (mg) | 1 limb | 2 limbs | 3 limbs | 4 limbs | |
| 10 | 20 | 40 | 60 | 80 | (dose a) |
| 7 | 14 | 28 | 42 | 56 | (dose b) |
| 3 | 6 | 12 | 18 | 24 | (dose c) |

TABLE 2

| Day | Glyceryl trinitrate mg | Glyceryl trinitrate total mg | Systolic Blood Pressure mmHg | Diastolic Blood Pressure mmHg | Mean Blood Pressure mmHG | Heart Rate beats/min | Obel Grade Lameness |
|---|---|---|---|---|---|---|---|
| 0 | | | 159 | 91 | 127 | 78 | 3.75 |
| 1 | 86.4 | 86.4 | 128 | 70 | 70 | 52 | 4 |
| 2 | 86.4 | 172.8 | 92 | 47 | 64 | 42 | 2.75 |
| 3 | 26.8 | 259.2 | 97 | 45 | 64 | 41 | 1.5 |
| 5 | 0 | 259.2 | 96 | 54 | 71 | 42 | 1 |

We claim:

1. A method for treating or controlling a disease or distress condition in a non-human mammal, the disease or distress condition selected from the group consisting of laminitis, acute equine rhabdomylosis or azoturia, navicular disease, chronic obstructive pulmonary disorder (COPD), exercise induced pulmonary hemorrhage (EIPH), loss of libido in breeding stallions, or vascular and myometrial complications associated with pregnancy, the method comprising the steps of:

topically applying to an affected limb of the mammal a therapeutically effective composition including a nitrovasodilator for treating or controlling the disease or distress condition and applying a protective covering or dressing comprising a cuff, sleeve, or boot for fastening to the limb of the non-human mammal.

2. The method of claim 1 wherein the nitrovasodilator comprises from about 0.5% to about 10% by weight of the composition.

3. The method of claim 1 wherein the nitrovasodilator is a compound selected from the group consisting of glyceryl trinitrate and sodium nitroprusside.

4. The method of claim 1 wherein the nitrovasodilator is dispersed in a lipophilic vehicle.

5. The method of claim 1 wherein the nitrovasodilator comprises a unit dose of from 2.5 mg to 30 mg of the nitrovasodilator.

6. A method for treating or controlling a disease or distress condition in a non-human mammal, the disease or distress condition selected from the group consisting of laminitis, acute equine rhabdomylosis or azoturia, navicular disease, chronic obstructive pulmonary disorder (COPD), exercise induced pulmonary hemorrhage (EIPH), loss of libido in breeding stallions, or vascular and myometrial complications associated with pregnancy, the method comprising the steps of:

topically applying to an affected limb of the mammal a composition comprising a therapeutically active agent formulated for topical application for treating or controlling the disease or distress condition, wherein the active agent is a nitrovasodilator in the amount of from about 0.5% to about 10% by weight of the composition, and wherein the nitrovasodilator is a compound selected from the group consisting of glyceryl trinitrate and sodium nitroprusside; and, applying a protective covering or dressing comprising a cuff, sleeve, or boot for fastening to the limb of the non-human mammal.

* * * * *